United States Patent
Odenkirchen

(12) 
(10) Patent No.: US 8,353,701 B2
(45) Date of Patent: *Jan. 15, 2013

(54) SALIVARY DUCT CONSTRICTION APPARATUS

(75) Inventor: Bernard W. S. Odenkirchen, Katwijk (NL)

(73) Assignee: Ultradent Products, Inc., South Jordan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/857,659

(22) Filed: Aug. 17, 2010

(65) Prior Publication Data

US 2010/0311009 A1    Dec. 9, 2010

Related U.S. Application Data

(63) Continuation of application No. 11/773,248, filed on Jul. 3, 2007, now abandoned, which is a continuation of application No. 11/468,696, filed on Aug. 30, 2006, now abandoned, which is a continuation of application No. 11/468,705, filed on Aug. 30, 2006, now abandoned, which is a continuation-in-part of application No. 11/208,897, filed on Aug. 22, 2005, now Pat. No. 7,320,597.

(51) Int. Cl.
*A61C 17/06* (2006.01)
(52) U.S. Cl. ........................................ 433/136; 606/157
(58) Field of Classification Search .................... 433/91, 433/136; 604/316; 248/205.8; 606/140, 606/157, 201, 204.15
See application file for complete search history.

(56) References Cited

U.S. PATENT DOCUMENTS

| | | | |
|---|---|---|---|
| 765,537 | A | 7/1904 | Abbott |
| 930,236 | A | 8/1909 | Schacht |
| 1,165,275 | A | 12/1915 | Montgomery |
| 1,683,119 | A | 9/1928 | Ziegler |
| 2,371,082 | A | 3/1945 | Vistreich |
| 2,510,184 | A | 6/1950 | Lynn |
| 2,752,680 | A | 7/1956 | Fredrik |
| 2,776,489 | A | 1/1957 | McGahee |
| 3,068,868 | A | 12/1962 | Joseph |
| 3,460,254 | A | 8/1969 | Scheuer |

(Continued)

FOREIGN PATENT DOCUMENTS

FR    2844700    3/2004

(Continued)

OTHER PUBLICATIONS

Title: Chirurgische behandeling van Aambeien (Hemorrhoiden) Inclusief foto's van behandeling URL: http://www.chirugenoperatie.nl/pagina/anus/aambeien.php, (copyright 2005).

(Continued)

*Primary Examiner* — Ralph Lewis
(74) *Attorney, Agent, or Firm* — Workman Nydegger

(57) ABSTRACT

A saliva control device for controlling saliva flow from a salivary duct without damaging the salivary duct and surrounding soft oral tissue includes an elastic body, a constriction hole formed through the elastic body, and an interior wall defining the constriction hole. The interior wall is substantially smooth and the elastic body sufficiently stretchable that the constriction hole expands during placement around a salivary duct and the wall constricts around the salivary duct to prevent flow of saliva without substantially cutting off blood flow to and damaging the salivary duct and soft oral tissue surrounding the salivary duct.

20 Claims, 11 Drawing Sheets

U.S. PATENT DOCUMENTS

| | | | |
|---|---|---|---|
| 3,682,175 | A | 8/1972 | Halter |
| 3,782,385 | A | 1/1974 | Loyd |
| 3,819,091 | A | 6/1974 | Hollender |
| 3,863,635 | A | 2/1975 | Swatman |
| 3,884,409 | A | 5/1975 | Kaufman |
| 4,033,346 | A | 7/1977 | Phillips |
| 4,114,605 | A | 9/1978 | McGhee et al. |
| 4,259,067 | A | 3/1981 | Nelson |
| 4,806,084 | A | 2/1989 | Neward |
| 4,828,491 | A | 5/1989 | Gray |
| 4,834,110 | A | 5/1989 | Richard |
| 4,954,054 | A | 9/1990 | Neward |
| 4,998,633 | A | 3/1991 | Schneider |
| 5,066,228 | A | 11/1991 | Doundoulakis |
| 5,115,816 | A | 5/1992 | Lee |
| 5,145,367 | A | 9/1992 | Kasten |
| 5,213,110 | A | 5/1993 | Kedem et al. |
| 5,277,557 | A | 1/1994 | Cooper |
| 5,478,216 | A | 12/1995 | Neward |
| 5,741,273 | A | 4/1998 | O'Regan |
| 5,865,827 | A | 2/1999 | Bullister |
| 6,213,772 | B1 | 4/2001 | Costello |
| 6,267,591 | B1 | 7/2001 | Barstow |
| 6,386,871 | B1 | 5/2002 | Rossell |
| 6,398,277 | B1 | 6/2002 | McDonald |
| 6,409,737 | B1 * | 6/2002 | Fortier et al. ............ 606/140 |
| 6,613,060 | B2 | 9/2003 | Adams et al. |
| 6,752,630 | B2 | 6/2004 | Roetzer |
| 6,979,184 | B2 | 12/2005 | Wu et al. |
| 7,320,597 | B2 * | 1/2008 | Odenkirchen ............ 433/91 |
| 2002/0138109 | A1 | 9/2002 | Keogh et al. |
| 2005/0014107 | A1 | 1/2005 | Culver |
| 2006/0008764 | A1 | 1/2006 | Abo |

FOREIGN PATENT DOCUMENTS

| | | |
|---|---|---|
| GB | 2322802 A | 9/1998 |
| JP | 09005322 | 1/1997 |
| JP | 09122156 | 5/1997 |
| SU | 1649592 | 5/1991 |
| WO | 03/068073 | 8/2003 |
| WO | 2004/069084 | 8/2004 |

OTHER PUBLICATIONS

Office Action dated Apr. 3, 2007 cited in related U.S. Appl. No. 11/468,705.

Office Action dated Apr. 3, 2007 cited in U.S. Appl. No. 11/208,897.

Notice of Allowance dated Sep. 27, 2007 cited in U.S. Appl. No. 11/208,897.

Office Action dated Oct. 9, 2009 cited in U.S. Appl. No. 11/773,248.

Office Action dated Apr. 1, 2010 cited in U.S. Appl. No. 11/773,248.

Notice of Allowance dated Jun. 28, 2010 cited in U.S. Appl. No. 11/773,248.

U.S. Appl. No. 11/468,696, filed Jul. 2, 2007, Office Action.

* cited by examiner

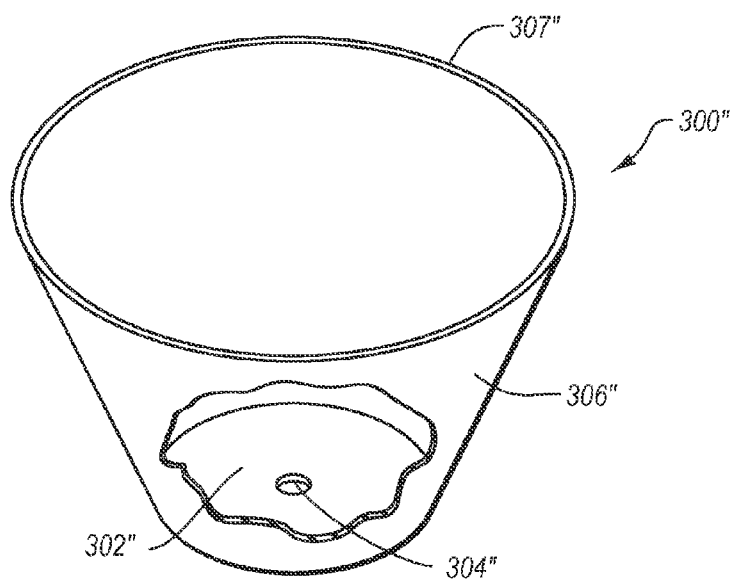
Fig. 3C
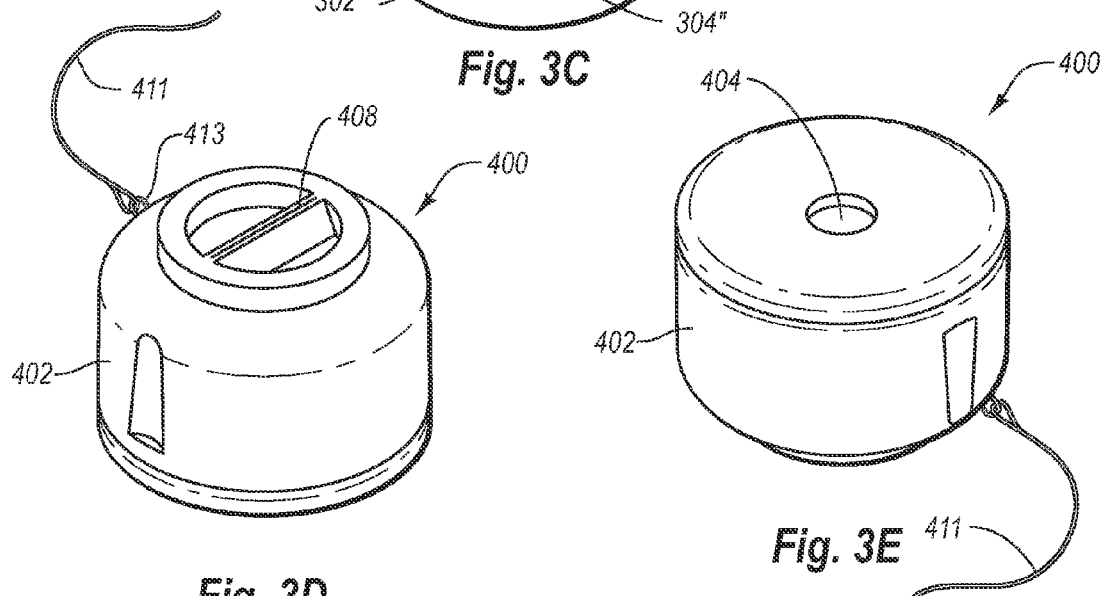
Fig. 3D
Fig. 3E
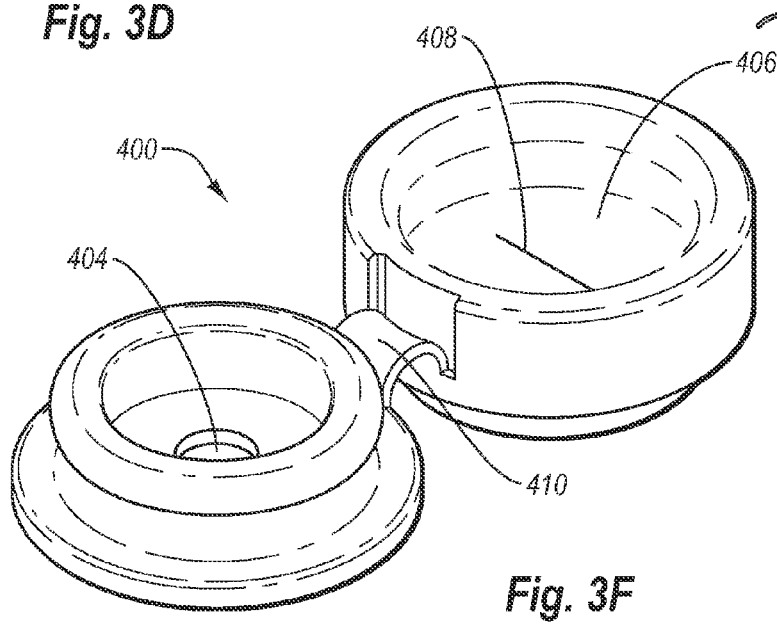
Fig. 3F

SALIVARY DUCT CONSTRICTION APPARATUS

RELATED APPLICATIONS

The present application is a continuation of co-pending U.S. patent application Ser. No. 11/773,248, filed Jul. 3, 2007, which is a continuation of co-pending U.S. patent application Ser. No. 11/468,696, filed Aug. 30, 2006 and a continuation of co-pending U.S. patent application Ser. No. 11/468,705, filed Aug. 30, 2006, which is a continuation-in-part of co-pending U.S. patent application Ser. No. 11/208,897, filed Aug. 22, 2005 and entitled "VACUUM SEALED SALIVA CONTROL DEVICE". The disclosures of the foregoing applications are incorporated in their entirety.

BACKGROUND OF THE INVENTION

1. The Field of the Invention

The present invention relates to saliva control devices and an integral hand-held vacuum pump apparatus for use in attaching one or more of the saliva control devices over a salivary duct so as to reduce or eliminate the flow and production of saliva. The saliva control devices and associated vacuum pump apparatus are particularly useful for a dental practitioner or oral surgeon (hereinafter practitioner) when performing a procedure within the oral cavity.

2. The Relevant Technology

When performing various procedures within the oral cavity, it is often desirable or necessary for the practitioner to slow or at least divert the flow of saliva produced by the salivary ducts. There are four principal salivary ducts within the oral cavity. The two parotid salivary ducts are located inside the mouth and near each ear. There are also two submandibular salivary ducts located on the floor of the mouth, near the base of the tongue. The vast majority of saliva produced enters a patient's mouth through these principal salivary ducts. A minor amount also enters through other auxiliary salivary ducts. Several devices and techniques have been employed in order to prevent saliva from interfering with a practitioner's work inside the oral cavity.

Rolls of cotton have been used in an attempt to prevent saliva produced by the principal salivary ducts from interfering with the work of a practitioner within the oral cavity. Cotton rolls are placed below the parotid salivary ducts and/or over the submandibular salivary ducts. As saliva is produced, it drains downward, and is absorbed by the cotton. One disadvantage of using cotton rolls is that they are rather large and can restrict the ability of the practitioner to work within the oral cavity because they take up considerable space. In addition, they can quickly become saturated, necessitating removal and replacement of the cotton during the procedure. It is often difficult to maintain the cotton roll in the position placed. Finally, cotton rolls can be uncomfortable for the patient.

Rubber dams have also been used for isolating an area of the mouth from saliva. Rubber dams are difficult to use as they must be assembled, which can take a significant amount of time. In addition, when using a rubber dam, the patient cannot completely close his or her mouth. This makes it difficult for the practitioner to check the patient's occlusion, and is generally uncomfortable for the patient.

Dental suction tubes have also been used to remove excess saliva produced by the salivary ducts. Generally, the suction tube is inserted periodically to remove excess saliva as it pools in the patient's mouth. This either requires an assistant to periodically insert the suction tube, or it requires interrupting the practitioner's work.

Systemic medications (e.g., scapolquinine and atropine) have been used to control the production of saliva. While useful in arresting saliva production, side effects include disorientation, amnesia, and lingering dry mouth. Furthermore, such medications typically require several minutes time after administration to begin working Improved saliva control devices have been developed by one of the present inventors which can be easily employed by a practitioner with a minimum of discomfort to the patient. Such devices are disclosed in copending U.S. application Ser. No. 11/208,897, filed Aug. 22, 2005, previously incorporated by reference. Generally, these saliva control devices are attached over the salivary duct and act to minimize or prevent the production and/or flow of saliva. The saliva control devices remain in place during the course of the practitioner's work within the oral cavity and are easily removed once work is completed.

During attachment of some of the saliva control devices over a salivary duct, a vacuum is needed in order to facilitate attachment of the device over the salivary duct. As such, it would be an improvement in the art to provide a specially designed hand-held vacuum pump apparatus for use in attaching saliva control devices over a salivary duct.

BRIEF SUMMARY OF THE INVENTION

The present invention is directed to systems including one or more saliva control devices and related methods for attaching the saliva control device to a salivary duct of a saliva producing salivary gland. The attached saliva control device advantageously prevents production and flow of saliva from a salivary duct while a practitioner works within the oral cavity of a patient.

The inventive system includes a saliva control device and means for applying a vacuum to a salivary duct so as to facilitate positioning of the saliva control device over the salivary duct. The saliva control device includes an elastic body comprising at least one elastomer and a constriction hole formed through the elastic body for constricting around a salivary duct. The stiffness of the elastic body and/or the diameter of the constriction hole advantageously are configured to provide a degree of constriction to a salivary duct upon attachment sufficient to prevent a flow of saliva without substantially cutting off blood flow to the tissue surrounding the salivary duct. In this way, saliva flow is blocked without damaging the tissue surrounding the salivary duct.

The inventive system and method allow a practitioner to position and attach a saliva control device over one or more selected principal salivary ducts located within a patient's mouth. Positioning and attachment of the saliva control devices is relatively quick and simple, and allows the practitioner to stop the production and flow of saliva while performing dental surgery or another procedure where the elimination of saliva within the oral cavity would be beneficial. The inventive system and method are improvements over existing suctioning, wicking, or absorbent devices used to remove saliva from the mouth, dams used to confine saliva to certain areas within the mouth, or drugs that biochemically stop the production and flow of saliva.

The means for applying a vacuum to a salivary duct so as to allow attachment of the saliva control device over the salivary duct may include a hollow suction tube and one of a plunger, a vacuum pump, or a hand-operated vacuum gun for producing a vacuum within the hollow suction tube. The hollow suction tube may be used to suction the raised nub of tissue surrounding a selected salivary duct into a distal end of the hollow suction tube so as to allow the practitioner to more easily position and attach the saliva control device over the salivary duct. The hollow suction tube may be inserted through the constriction hole so as to temporarily enlarge the constriction hole as the saliva control device is placed on the tube. The saliva control device may then be slid distally off the end of the hollow suction tube, in place over the salivary duct. In another method, the saliva control device may be friction fitted or held by vacuum force against the distal end of the hollow suction tube while the raised nub of tissue is suctioned through the constriction hole and into the hollow suction tube. In either case, because of the elasticity of the elastic body surrounding the constriction hole, the elastic body springs closed around the salivary duct so as to prevent production and flow of saliva from the salivary duct.

The saliva control device may remain in place as long as necessary, typically between about 10 minutes and about 3 hours, after which the saliva control device is removed. The elastic body of the saliva control device may comprise a substantially flat disc, and in order to more easily facilitate removal of the device, the elastic body may further include one or more ear-like protrusions, one or more slits, or one or more cut-outs to provide an edge which can be more easily gripped by the practitioner so as to allow for easy removal of the device when desired An integral hand-held vacuum pump apparatus may be used in attaching one or more saliva control devices over one or more selected salivary ducts. The vacuum pump apparatus can be operated by a single hand of a practitioner in order to adhere a saliva control device, e.g., by drawing a portion of a salivary duct into an orifice of a saliva control device by suction.

The pump apparatus includes a body having a grippable handle and a support member, a hollow suction tube that is supported by the support member of the body, a plunger slidably disposed within the hollow suction tube, and means for moving the plunger proximally within the hollow suction tube in response to squeezing a practitioner's hand and/or at least one finger. An example of such means includes a finger grippable lever which when squeezed causes the plunger to slide proximally within the hollow suction tube so as to create a vacuum within the hollow suction tube. Release of the plunger releases the vacuum.

At least a portion of the finger grippable lever is spaced apart from the grippable handle of the body, and the lever is also movably mounted to the grippable handle such that the lever may be selectively squeezed or otherwise moved relative to the handle. The lever is operatively coupled to the plunger so as to cause the plunger to slide proximally within the hollow suction tube when the lever is squeezed, resulting in the creation of a vacuum suction force within the hollow suction tube. Depending on the configuration of the saliva control device to be attached, the vacuum can advantageously be used to vacuum adhere the device over a salivary duct, or in another embodiment, the vacuum can advantageously be used to suction up the nub of tissue surrounding the salivary duct, after which the saliva control device can be positioned so as to constrict around the salivary duct, effectively cutting off saliva flow. The vacuum is released (e.g., by releasing force on the lever), after which the pump apparatus is detached from the saliva control device and removed from the patient's mouth The integral hand-held vacuum pump apparatus advantageously requires no connection to an external vacuum source. In other words, no cords or tubes run from the apparatus at one end to an external vacuum source at another end as in, e.g., a corded dental suction tool. The elimination of cords or tubes greatly improves the maneuverability of such an apparatus relative to devices that require connection to an external vacuum source. This maximizes the ability of the practitioner to manipulate the device into a desired one of many possible positions so as to ensure proper placement of the saliva control device. Because the apparatus is self-contained and manually actuable to create a vacuum, no external connection is needed, and the necessary vacuum is generated within the hand-held apparatus itself (e.g., by squeezing the lever).

The hollow suction tube may be detachable from the rest of the apparatus to facilitate changing of the tube between patients (e.g., the hollow suction tube may be disposable) so as to prevent or minimize the possibility of cross-contamination between patients. The remainder of the apparatus advantageously may be easily washed or disinfected by autoclaving, as needed.

These and other benefits, advantages and features of the present invention will become more full apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIG. 3C illustrates another alternative embodiment of a saliva control device including an elongated outwardly flared sidewall;

FIGS. 3D and 3E are top and bottom views, respectively, of an alternative saliva control device;

FIG. 3F is a perspective view of the device of FIGS. 3D-3E with the device in an open position so as to allow viewing into the interior of the saliva control device;

DETAILED DESCRIPTION OF THE PREFERRED EMBODIMENTS

I. Introduction

The present invention is directed to an integral (i.e., self-contained) hand-held vacuum pump apparatus for use in attaching one or more saliva control devices over one or more selected salivary ducts. The inventive hand-held vacuum pump apparatus allows a practitioner to easily install one or more saliva control devices over one or more salivary ducts so as to control production and flow of saliva into the oral cavity during dental surgery or another procedure where elimination of saliva would be advantageous. The apparatus can be operated using a single hand.

II. Exemplary Saliva Control Devices

Figure 1:
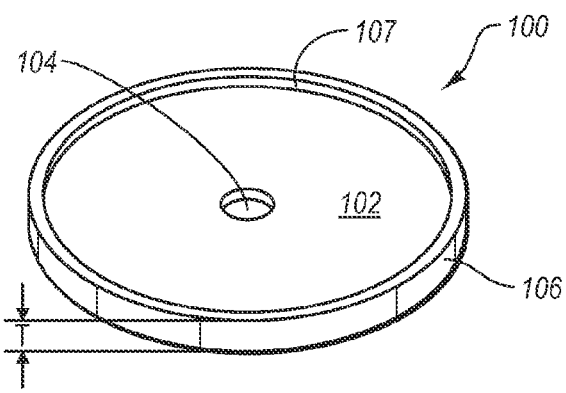
FIG. 1 is a perspective view of an exemplary saliva control device.

FIG. 1 illustrates one exemplary saliva control device 100 including an elastic body 102 and an opening in the form of constriction hole 104 formed near the center of elastic body 102. Elastic body 102 is illustrated as comprising a substantially flat, planar circular disc having a bottom surface for placement against oral tissue surrounding a salivary duct, with constriction hole 104 formed through the bottom surface of body 102, although other configurations are possible (e.g., oval, rectangular, etc.). Illustrated saliva control device 100 advantageously includes an optional raised rim 106 extending around an outer perimeter of elastic body 102. As illustrated, rim 106 has a cross sectional thickness T (i.e., height) that is greater than the cross sectional thickness of the elastic body 102 adjacent to constriction hole 104. Optional rim 106 advantageously adds an additional degree of rigidity to device 100, which is helpful during handling and placement of the device, particularly when inserting a tissue nub surrounding a selected salivary duct through constriction hole 104. In addition, the interior surface 107 of rim 106 advantageously provides a surface against which the hollow suction tube of the hand-held vacuum pump apparatus can friction fit (i.e., the tube can friction within the interior space defined by interior surface 107 of outer rim 106. This mating configuration will be described in further detail below.

Elastic body 102 is advantageously formed from one or more elastomeric materials (e.g., a thermoplastic elastomer). Suitable elastomers include various polyolefins (e.g., polypropylene and polyethylene), latex, and styrene-ethylene-butylene-styrene (SEBS) copolymer. Any suitable elastomeric material may be used, so long as it is non-toxic when used within the oral cavity, and provides a sufficient degree of stretchability. Preferably, the selected elastomeric material has a stretchability of at least about 200 percent, more preferably at least about 400 percent, and most preferably at least about 800 percent.

The diameter of constriction hole 104 and/or the stiffness and stretchability of elastic body 102 are advantageously configured so as to provide a degree of constriction to a salivary duct sufficient to stop the flow of saliva without substantially cutting off blood flow within the tissue nub surrounding the salivary duct when the tissue nub is inserted through the constriction hole (i.e., when the elastic body springs closed or otherwise constricts around the tissue nub surrounding the salivary duct). Constriction hole diameters between about 0.1 mm and about 2 mm, more preferably between about 0.5 mm and about 1.75 mm, and most preferably between about 0.8 mm and about 1.5 mm have been found to be satisfactory. The selected diameter depends on the stiffness versus the stretchability of the material, among other physical properties. Relatively larger diameters may be used with materials having lower stretchability values. In other words, if the elastic body is formed of a material having relatively low stretchability (i.e., high stiffness), the constriction hole diameter may be relatively large (e.g., slightly smaller than a diameter of the tissue nub of a salivary duct). Conversely, if the elastic body is formed of a material having relatively high stretchability (e.g., at least about 500 percent), the constriction hole diameter may be relatively small (e.g., less than about 0.8 mm).

Figure 2:
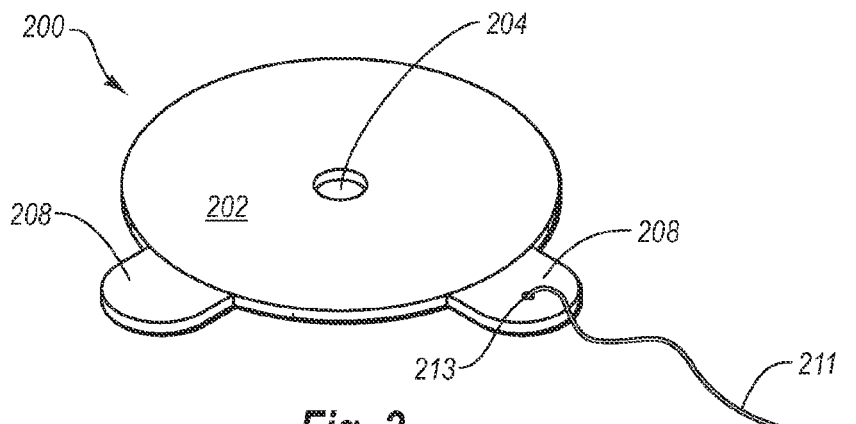
FIG. 2 illustrates an alternative saliva control device including a plurality of ear-like protrusions.

FIG. 2 illustrates an alternative saliva control device 200 including an elastic body 202, and a constriction hole 204. One principal difference between the device 100 of FIG. 1 and the device 200 of FIG. 2 is that the device 200 includes ear-like protrusions 208 which advantageously provide a more easily accessible gripping surface for facilitating easier removal of the device. In other words, ear-like protrusions 208 provide an edge surface which is more easily gripped. In addition, the device 100 of FIG. 1 includes optional rim 106 whereas no such rim is illustrated as a part of the device 200 of FIG. 2 (although such a rim may optionally be included).

Saliva control device 200 is illustrated as advantageously including an optional lifeline (or leash) 211 to prevent device 200 from inadvertently falling down the patient's throat or being inhaled. One end of lifeline 211 is attached to device 200, such as through a depression or protrusion (e.g., through eyelet 213), and the other end is attached to any suitable anchor (e.g., a dental device external to the patient's mouth) so as to prevent device 200 from being swallowed, choked on, inhaled, or otherwise lost in the event it becomes detached from the inside of the patient's mouth. Examples of suitable lifeline materials include ordinary string, dental floss, and monofilament. Although illustrated in conjunction with device 200 of FIG. 2, it will be understood that any inventive saliva control device within the scope of the invention may advantageously be configured for use with a lifeline.

Figures 3A, 3B:
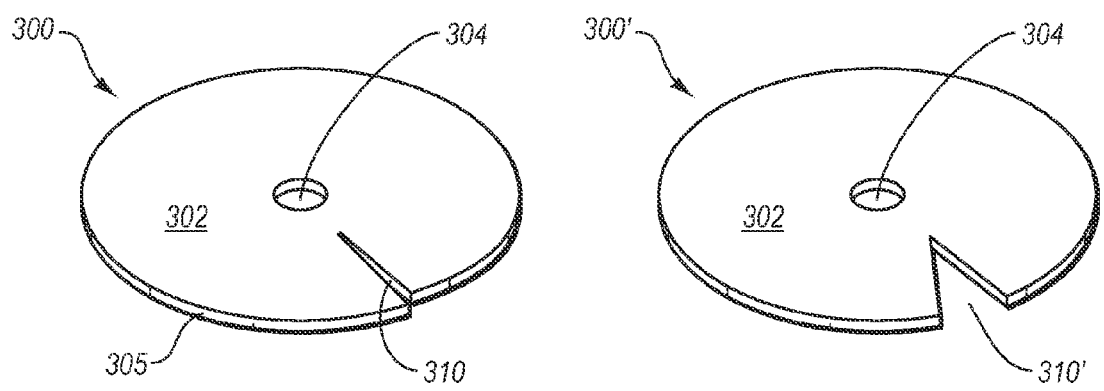
FIGS. 3A and 3B illustrate additional alternative embodiments of saliva control devices including a slit and a cut-out, respectively.

FIGS. 3A and 3B illustrate two additional alternative embodiments. Saliva control device 300 of FIG. 3A includes an elastic body 302 and a constriction hole 304. Device 300 of FIG. 3A further includes a slit 310 extending from outer edge 305 of elastic body 302 towards constriction hole 304. Advantageously, slit 310 does not extend the full distance to constriction hole 304, which allows elastic body 302 to be capable of providing a sufficient degree of constriction to a salivary duct. Similar to ear-like protrusions 208 of the embodiment illustrated in FIG. 2, slit 310 also provides a surface that is more easily gripped by the practitioner so as to allow for simple removal of the device once the practitioner has finished working within the oral cavity of a patient.

FIG. 3B illustrates an alternative embodiment of a saliva control device 300' also including an elastic body 302 having a constriction hole 304 formed near the center of elastic body 302. Rather than a simple slit, device 300' includes a cut-out 310'. For example, a pie-slice shaped cut-out portion 310' of elastic body 302 is illustrated as having been removed. Such a configuration similarly provides an edge surface which can be easily gripped by the hand of the practitioner or through the use of a tool manipulated by the practitioner to allow for easier removal of the device when needed.

FIG. 3C illustrates another alternative embodiment of a saliva control device 300" including an elastic body 302" having a constriction hole 304" formed near the center of elastic body 302". Advantageously, device 300" further includes an outwardly flared sidewall 306" that terminates at an upper rim 307". Sidewall 306" and upper rim 307" provide a surface that is more easily gripped by the practitioner (as compared to only the relatively small elastic body 302") so as to allow for simple removal of the device once the practitioner has finished working within the oral cavity.

Device 300" provides a further advantage when placing two devices in close proximity to each other (e.g., when one device is placed over each of the two submandibular salivary ducts on the floor of the mouth) because the bottom of the device (i.e., elastic body 302") can be relatively small, for example about 4 mm or less in diameter. Upper rim 307" may be much larger, e.g., about 6-8 mm or more in diameter. Such a configuration allows for close proximity placement of two devices because of the small size of the bottom elastic body portion, while also providing a larger diameter at upper rim 307" for easy gripping. Advantageously, the height of sidewall 306" may be less than about 10 mm, preferably less than about 7 mm, which is particularly useful when the device is placed under the tongue, over one of the submandibular salivary ducts. A relatively short sidewall (e.g., less than about 7 mm) is more comfortable for the patient as the device doesn't substantially interfere with the relaxed placement of the patient's tongue. Sidewall 306" is advantageously flexible so that the elastic body bases of two devices may be placed next to each other, with the flexible sidewalls flexing to accommodate each other (e.g., as may be necessary when placing the devices over the two close-together submandibular salivary ducts, which are typically 1-7 mm apart). In one embodiment, sidewall 306" may be formed of the same elastomeric material as elastic body 302".

FIGS. 3D-3F illustrate an exemplary saliva control device 400. FIGS. 3D and 3E illustrate top and bottom perspective views, respectively, while FIG. 3F illustrates a perspective view with the device 400 in an open position so as to better see the interior of the device. Device 400 includes a body 402, a cavity (i.e., an opening or hole) 404, a vacuum chamber 406, and an air evacuation passage (e.g., a one way valve) 408. A lifeline (or leash) 411 may advantageously be included to prevent the device 400 from inadvertently falling down the patient's throat or being inhaled. One end of the lifeline 411 is attached to device 400, such as through a depression or protrusion (e.g., through eyelet 413), and the other end is attached to any suitable anchor (e.g., a dental device external to the patient's mouth) so as to prevent device 400 from being swallowed, choked on, inhaled, or otherwise lost in the event it becomes detached from the inside of the patient's mouth. Examples of suitable lifeline materials include ordinary string, dental floss, and monofilament. Although illustrated as being substantially circular in FIGS. 3D-3F, the body 402 and cavity 404 may be of any desired shape.

Cavity 404 is configured for forming a seal over a salivary duct. In other words, device 400 is configured for vacuum adhering over a selected salivary duct. The cavity 404 formed in the body 402 forms a seal over the salivary duct, while vacuum chamber 406 and air evacuation passage 408 assist the cavity in forming a seal. Air evacuation passage 408 is in fluid communication with vacuum chamber 406, which is in communication with cavity 404. A vacuum is applied to air evacuation passage 408, which creates and maintains a vacuum within the vacuum chamber 406 and cavity 404. The device is positioned over a selected salivary duct, a reduced pressure is applied through passage 408 to chamber 406 and cavity 404, and the salivary duct is pulled into cavity 404. According to one embodiment, cavity 404 is sufficiently small such that when the salivary duct is pulled up into cavity 404 the salivary duct is constricted between the walls of the body defining the opening 404. In this way the device reduces production of saliva and/or prevents saliva produced by the salivary duct from flowing beyond the confines of the device. According to one embodiment, the body 402 surrounding cavity 404 may be formed of a soft, adaptable material. In addition to forming a tight seal, a soft flexible material may provide a higher degree of comfort for the patient.

Air evacuation passage 408 is configured so as to allow selective evacuation of air from vacuum chamber 406 and cavity 404, allowing the practitioner to vacuum adhere device 400 over a person's salivary duct. The saliva control device may be formed as a single integral piece. As illustrated in FIG. 3F, body 402 may comprise two integral portions connected together by a flexible hinge 410. In the illustrated embodiment air evacuation passage 408 comprises a one way slit valve although other configurations may be used.

Additional embodiments and more details regarding device 400 are disclosed in U.S. patent application Ser. No. 11/208,897 filed Aug. 22, 2005 and entitled "VACUUM SEALED SALIVA CONTROL DEVICE," already incorporated by reference. Additional embodiments and more details of the saliva control device 100 illustrated in FIG. 1 are disclosed in U.S. patent application Ser. No. 11/468,696 filed Aug. 30, 2006 and entitled "SALIVARY DUCT CONSTRICTION DEVICES SYSTEMS AND METHODS". Still additional saliva control devices which may be used with the pump apparatus of the present invention are disclosed in PCT Patent Application Publication No. WO 2004069084 entitled "VACUUM SEALED SALIVA CONTROL DEVICE." Each of the above mentioned applications is hereby incorporated by reference.

III. Exemplary Systems And Methods Of Use

Figure 4A:
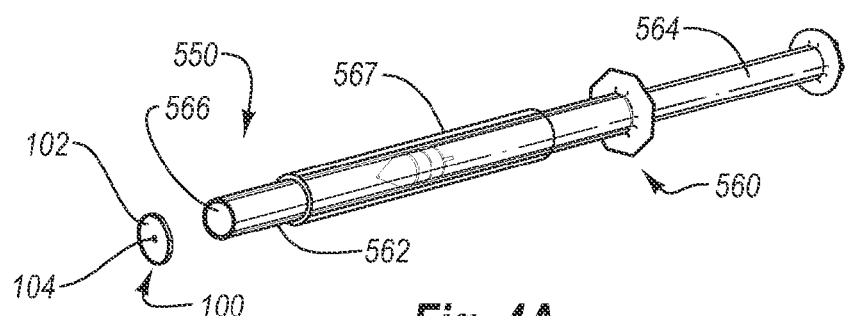
FIGS. 4A-4D illustrate an exemplary system including the saliva control device of FIG. 1 and a syringe including a hollow suction tube and a plunger.

FIG. 4A illustrates a system 550 including saliva control device 100 and a syringe 460 including a hollow suction tube 562 and a plunger 564. Syringe 560 may also optionally include an outer tube 567 which is slidable over hollow suction tube 562. Hollow suction tube 562 and plunger 564 are one example of means for applying a vacuum to a salivary duct so as to allow positioning of a salivary duct through the constriction hole 104 of elastic body 102. In use, the hollow suction tube 562 and plunger 564 may be used to suction a raised tissue nub surrounding a salivary duct up into hollow suction tube 562, after which the device 100 may be positioned so that the tissue nub surrounding the salivary duct is inserted through constriction hole 104 of elastic body 102.

Figure 4B:
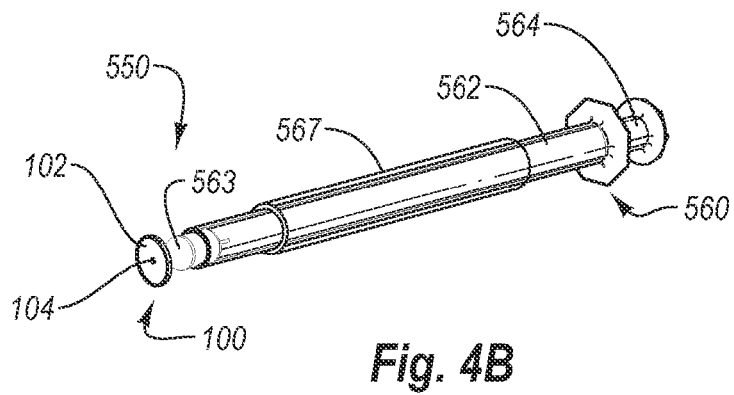

In one such kit, device 100 may be stored connected to syringe 560. For example, as illustrated in FIG. 4B, the distal end 563 of plunger 564 may have a conical configuration so as to terminate in a point. Device 100 may be fitted over the distal end of plunger 564 with little or no deformation of constriction hole 104. This may be advantageous when shipping and storing the kit as stretching the constriction hole substantially may result in the hole being rendered permanently larger, making it unsuitable for use after being stored. In other words, fitting constriction hole 104 over the point at distal end of plunger 564 requires little or no stretching of the hole, which may prevent permanent deformation that might otherwise occur.

Figure 4C:
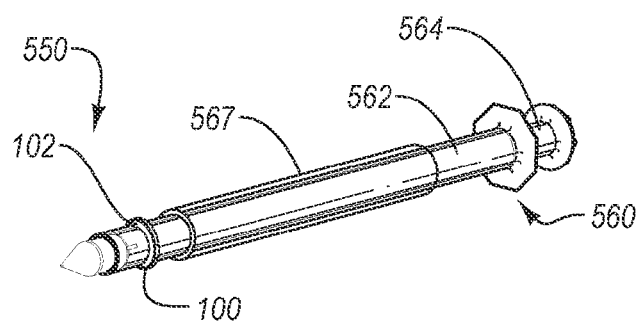
Figure 4D:
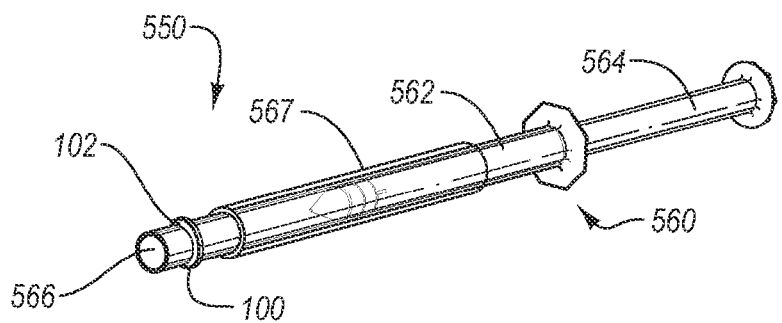

Once installation of device 100 over a salivary duct is desired, device 100 may easily be slid proximally up the distal end 563 of plunger 564 and over the distal end of hollow suction tube 562 by temporarily stretching constriction hole 104 to be large enough to insert the distal end of hollow suction tube 562 through constriction hole 104, as seen in FIG. 4C. Distal orifice 566 of hollow suction tube 562 may then be positioned over a selected salivary duct, and plunger 564 may be slid proximally (i.e., rearwardly) so as to create a vacuum within hollow suction tube 562 (see FIG. 4D). The tissue nub surrounding the selected salivary duct is suctioned into distal orifice 566 and hollow suction tube 562. Device 100 may then be slid distally over distal orifice 566, while the tissue nub of the selected salivary duct is still held within hollow suction tube 562. Syringe 560 may advantageously include an outer tube 567 which is slidably disposed over hollow suction tube 562 for forcing device 100 over distal orifice 566. Tweezers, the practitioner's fingers, or another dental tool may alternatively be used to slide device 100 distally over distal orifice 566. Once device 100 is slid off distal orifice 566, elastic body 102 springs closed because of the elasticity of elastic body 102 surrounding constriction hole 104. The result is that the base of the tissue nub becomes inserted through constriction hole 104. The vacuum within hollow suction tube 562 may then be released (e.g., by sliding plunger 564 distally or by pulling syringe 560 away so as to release the tissue nub held within hollow suction tube 562).

Figure 10A:
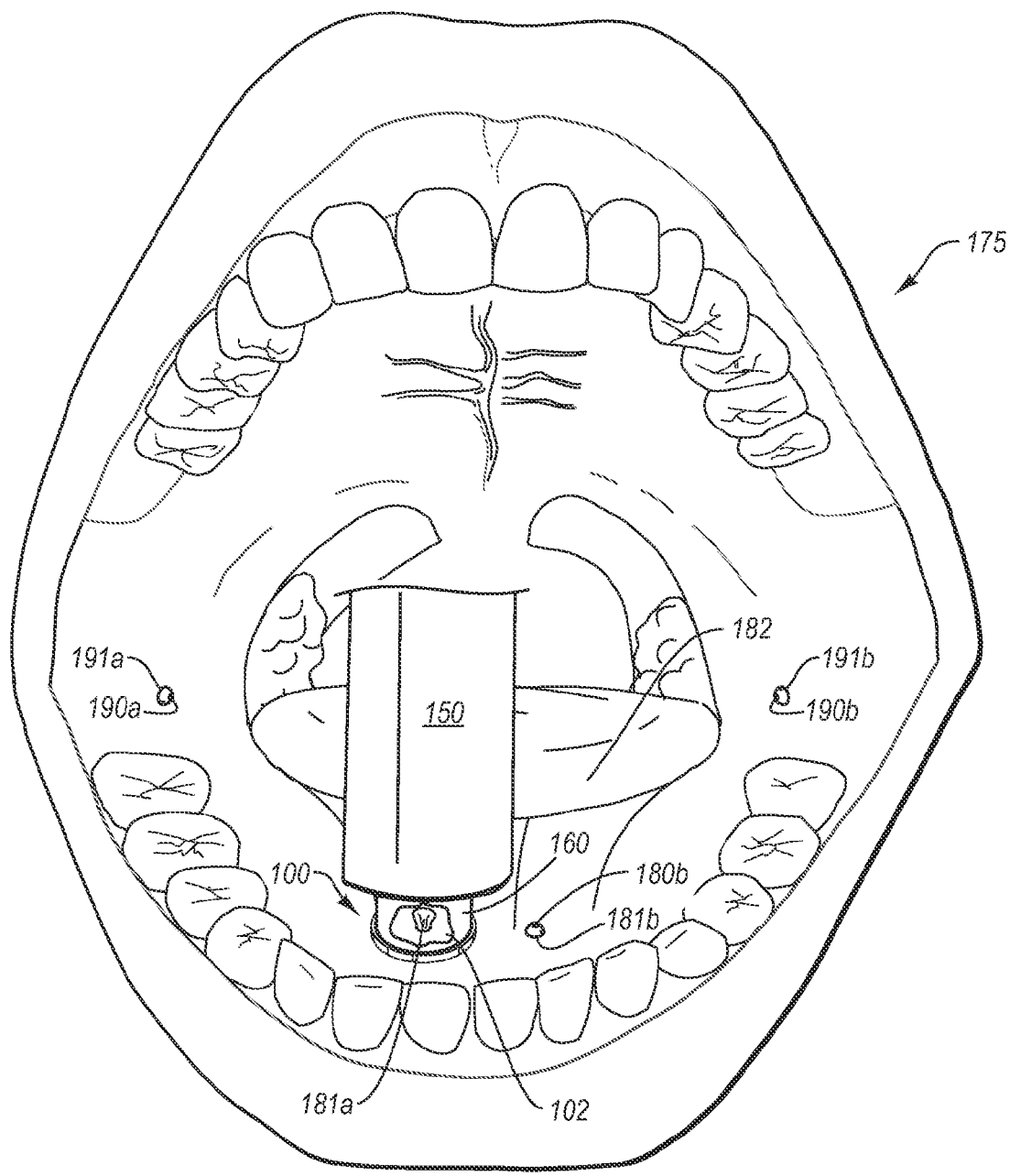
FIG. 10A illustrates placement of a saliva control device with the hand-held vacuum pump apparatus of FIG. 5.
Figure 10B:
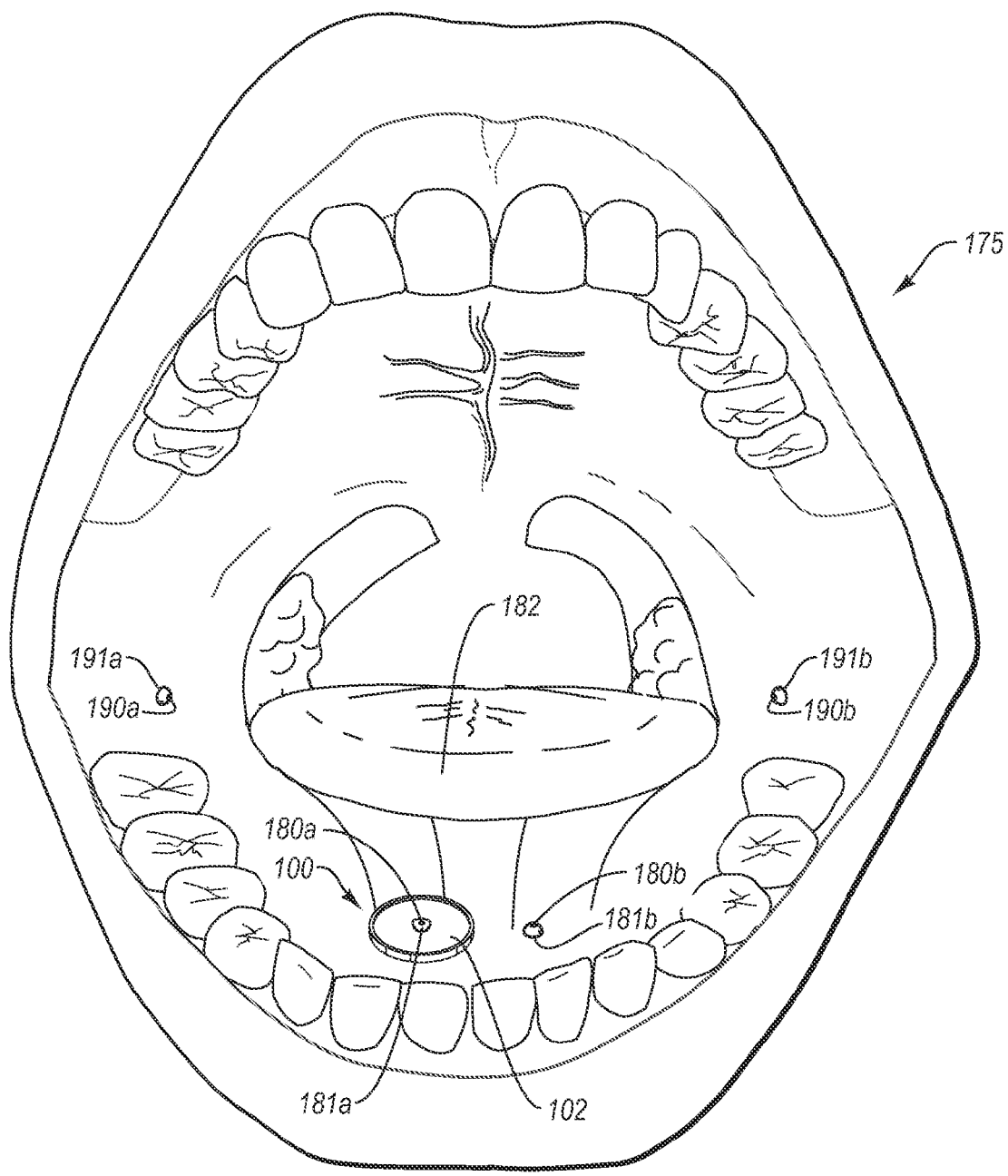
FIG. 10B illustrates a saliva control device in place over the salivary duct so as to prevent production and flow of saliva out of the salivary duct to which it is attached.

The tissue nub surrounding the salivary duct is squeezed by elastic body 102 surrounding constriction hole 104 (see FIG. 10B). Elastic body 102 constricts around the tissue nub of the salivary duct so as to prevent a flow of saliva from the salivary duct. Advantageously, the degree of constriction may be sufficient to prevent saliva production and flow, but not so great as to substantially cut off blood flow to the tissue nub (i.e., the tissue nub remains red because of blood flow). The degree of constriction is dependent on the diameter of constriction hole 104 and the stretchability of the material from which elastic body 102 is formed.

Figure 4E:
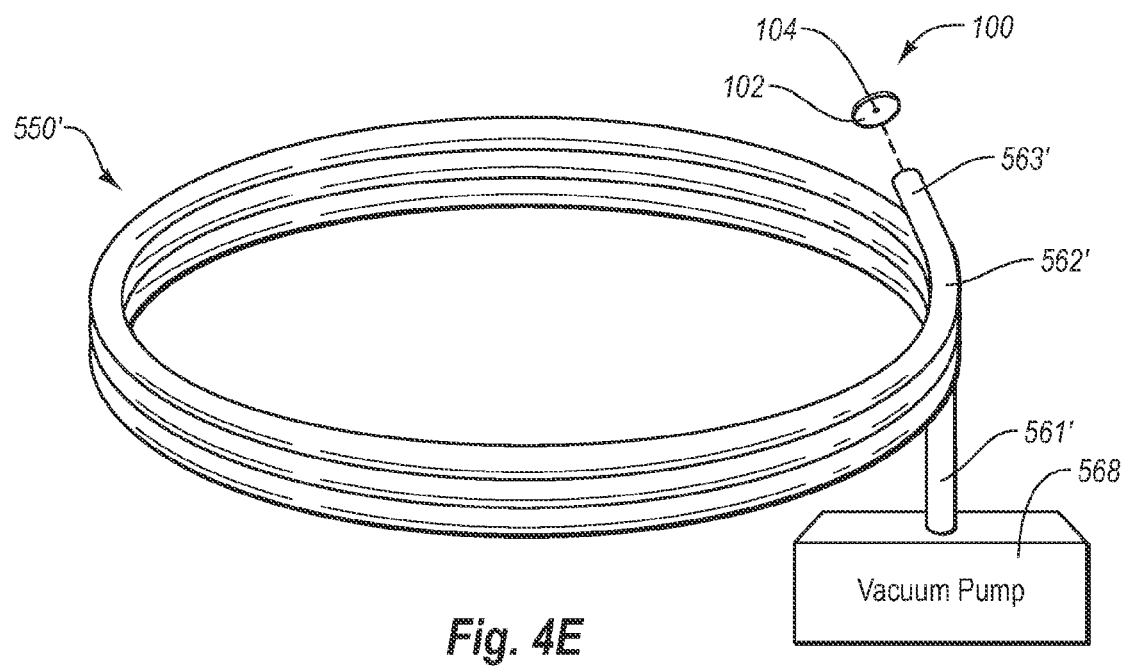
FIG. 4E illustrates an alternative system including the saliva control device of FIG. 1 and a hollow suction tube attached to a vacuum pump.

FIG. 4E illustrates an alternative system 550' including saliva control device 100, a hollow suction tube 562' which may comprise a length of flexible tubing (e.g., surgical tubing), and a vacuum pump 568 operationally coupled to a proximal end 561' of hollow suction tube 562'. Hollow suction tube 562' and vacuum pump 568 comprise another example of means for applying a vacuum to a salivary duct so as to allow attachment of the saliva control device to the salivary duct. In other words, hollow suction tube 562' and vacuum pump 568 allow for application of a vacuum within hollow suction tube 562' for suctioning up a tissue nub surrounding a selected salivary duct so as to allow insertion of the salivary duct through constriction hole 104 of elastic body 102.

Device 100 may be placed over distal end 563' of hollow suction tube 562' by stretching constriction hole 104 to be temporarily large enough to insert distal end 563' of hollow suction tube 562' through hole 104. The orifice at distal end 563' may then be positioned over a selected salivary duct, while vacuum pump 568 is active so as to create a vacuum within hollow suction tube 562'. The tissue nub surrounding the salivary duct is suctioned into hollow suction tube 562'. Device 100 may then be slid distally off hollow suction tube 562' while the tissue nub is still held within hollow suction tube 562', forcing the tissue nub to become inserted through constriction hole 104. Vacuum pump 568 may be turned off and hollow suction tube 562' removed. The tissue nub surrounding the salivary duct is squeezed by elastic body 102 surrounding constriction hole 104 so as to advantageously prevent the flow of saliva.

Alternatively, rather than temporarily enlarging constriction hole 104 and inserting distal end 563' through hole 104, the vacuum within hollow suction tube 562' may be used to hold device 100 against digital end 563' of hollow tube 562'. The orifice at distal end 563' and constriction hole 104 may then be positioned over a selected salivary duct, while vacuum pump 568 is active so as to create a vacuum within hollow suction tube 562' and through constriction hole 104. The tissue nub surrounding the salivary duct is suctioned through constriction hole 104 and into hollow suction tube 562'. Vacuum pump 568 may be turned off and hollow suction tube 562' removed. The tissue nub surrounding the salivary duct is squeezed by elastic body 102 surrounding constriction hole 104 so as to advantageously prevent the flow of saliva.

Figure 5:
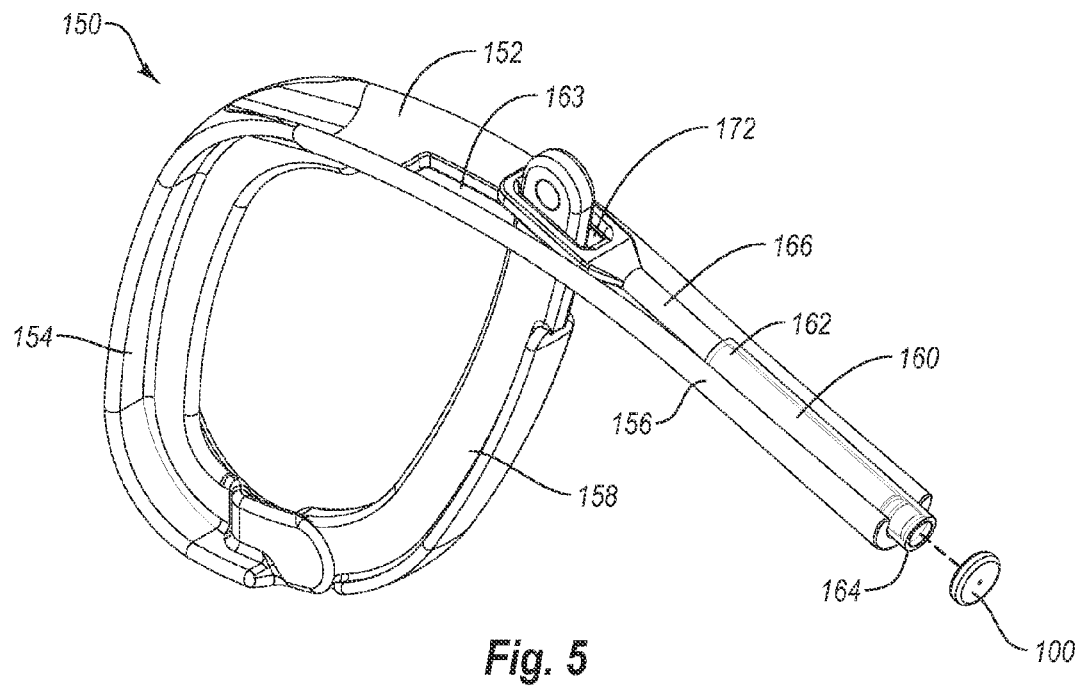
FIG. 5 is a perspective view of another alternative system using a hand-held vacuum pump apparatus for use in attaching a saliva control device over a salivary duct.

FIG. 5 illustrates another alternative system including saliva control device 100, a hollow suction tube 160, and a hand-operated vacuum gun 150 operationally coupled to a proximal end 162 of hollow suction tube 160. Hand-operated vacuum gun 150 includes a body having a grippable handle 154 and a cradle member 156, and a finger grippable lever 158 spaced apart from handle 154 that is movably mounted to handle 154 so that the user can grip and move lever 158 relative to handle 154. The hollow suction tube 160 is supported by cradle member 156, and a plunger 166 is slidably disposed within proximal end 162 of hollow suction tube 160. A proximal end of plunger 166 includes a slot 172 through which an end of lever 158 is disposed. Such a configuration produces a vacuum within hollow suction tube 160 when the user grips handle 154 and pulls finger grippable lever 158 towards handle 154 as plunger 166 slides proximally within tube 160.

Device 100 may be placed over tube 160 as described above by temporarily stretching constriction hole 104 over tube 160, although in a preferred alternative, tube 160 may have an outside diameter advantageously sized slightly larger than the inside diameter of rim 106 (see FIG. 1) of device 100 so that distal end 164 of tube 160 may friction fit within the inside diameter surface of rim 106. Such a configuration allows the practitioner to place and hold device 100 at distal end 164 of tube 160 prior to and during attachment of device 100

IV. Exemplary Integral Hand-Held Vacuum Pump Apparatuses

Figure 6:
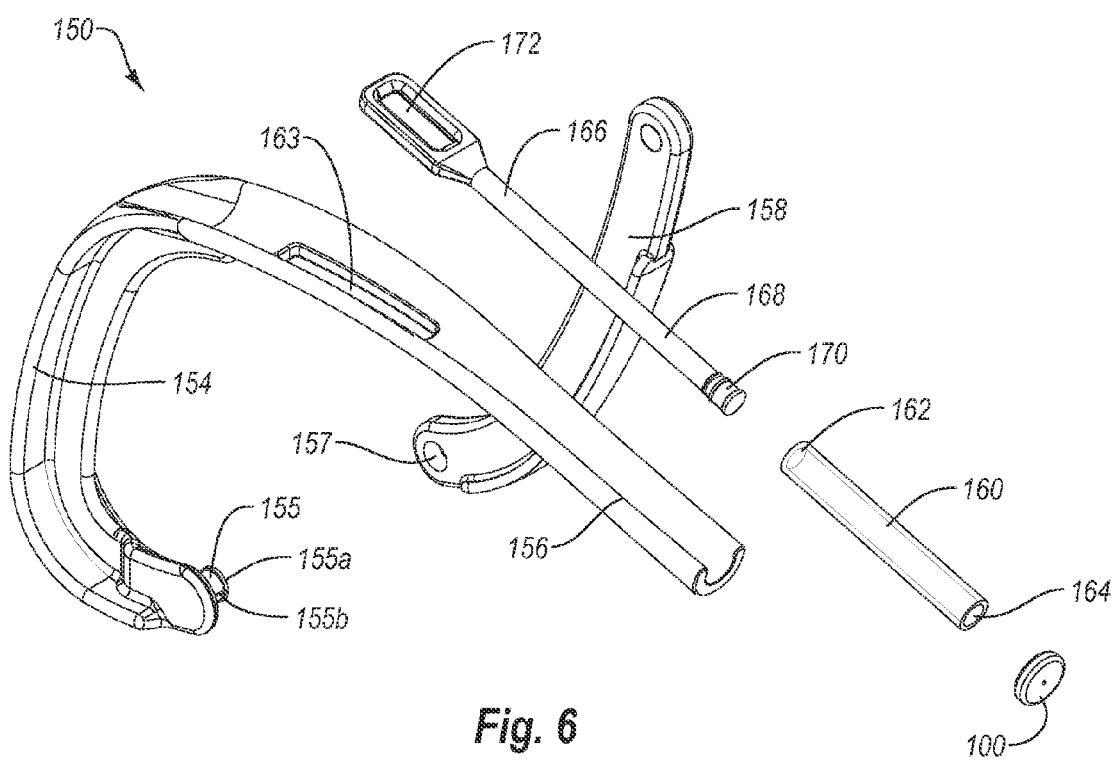
FIG. 6 is an exploded view of the vacuum pump apparatus of FIG. 5.

FIGS. 5 and 6 illustrate an exemplary integral hand-held vacuum pump apparatus 150. FIG. 5 shows a perspective view, while FIG. 6 is an exploded view of apparatus 150. As illustrated, vacuum pump apparatus 150 includes a body 152 having a grippable handle 154 and a support member, e.g., cradle 156. A finger grippable lever 158 is spaced apart from and substantially parallel to grippable handle 154. Lever 158 is an example of means for moving the plunger proximally within the hollow suction tube in response to squeezing a practitioner's hand and/or at least one finger. Grippable lever 158 is movably mounted to grippable handle 154 such the finger grippable lever 158 may be selectively moved relative to grippable handle 154. Positioning lever 158 so as to be substantially parallel to handle 154 facilitates easy gripping of both the handle and lever with a single hand, and provides for efficient, simple, and comfortable operation with a single hand. In the illustrated embodiment, handle 154 includes a pivot pin 155 (FIG. 6) configured to be received within a hole 157 formed near an end of lever 158. Pivot pin 155 may be secured within hole 157 by a snap fit. For example, the end of pin 155 opposite its base where it is attached to handle 154 may include an enlarged ridge 155a and a slit 155b so as to allow the pin 155 and enlarged ridge 155a to flex together. When flexed together, the effective diameter of pin 155 is reduced, and pin 155 including enlarged ridge 155a can be inserted through hole 157. Once fully inserted, ridge 155a and slit 155*b* spring back to their original unflexed configuration, locking pin 155 within hole 157.

A hollow suction tube 160 is supported by cradle support member 156 (e.g., having a U-shaped cross section so as to support and cradle tube 160). Hollow suction tube 160 includes a proximal end 162 and a distal end 164. A plunger 166 is slidibly disposed within hollow suction tube 160. Plunger 166 includes a stem 168 and a sealing plug 170 (FIG. 6). The sealing plug 170 and at least a portion of stem 168 are slidibly disposed within hollow suction tube 160. Tube 160 may advantageously be soft and flexible, making it comfortable and easily maneuverable within the mouth of a patient, while cradle 156 provides any necessary support and/or rigidity.

Cradle 156 is an example of a support member for supporting tube 160. The support member may be of any configuration capable of supporting tube 160. Cradle 156 partially surrounds and supports nearly the full length of tube 160, although alternative support members may surround the more or less of the circumference of tube 160 along any desired length and be of any configuration, so long as the support member is able to provide support to tube 160. Tube 160 may advantageously extend distally past the distal end of cradle 156 (e.g., about 1 cm or less), which is advantageous when using tube 160 to position a saliva control device 100 over a salivary duct, as it prevents the support member from interfering with maneuvering and/or positioning. Furthermore, it may be advantageous to form tube 160 of a transparent material so that the practitioner can more easily see when placing the tube and a saliva control device (e.g., device 100) over a salivary duct. In other words, a transparent tube allows a practitioner to more easily determine whether the tube and saliva control device are oriented correctly with respect to the salivary duct. For these same reasons, it may be advantageous in some embodiments for the saliva control device to also be transparent. Hollow suction tube may be formed of a suitable flexible, soft, adaptable thermoplastic material. Examples of suitable materials include various polyolefins, for example polypropylene.

Plunger 166 is operatively coupled at its proximal end to lever 158. In the illustrated embodiment, the coupling means comprises a slot 172 into which an end of lever 158 is inserted. This configuration provides that selective movement of lever 158 (i.e., pulling it towards handle 154) causes plug 170 to slide proximally within hollow suction tube 160 so as to create a vacuum within tube 160. The vacuum can be released by releasing lever 158, permitting distal movement of plug 170 within tube 160. The sliding movement of lever 158 is guided by a second slot 163 formed within body 152 through which lever 158 is also inserted so as to result in a smooth and guided feel for the practitioner during use. Such a smooth and guided feel is advantageous as it allows the practitioner to concentrate on positioning and placement of the saliva control device rather than the operation of the vacuum pump apparatus. In addition, the apparatus can advantageously be operated with a single hand, leaving the other hand free for other needs.

The body 152, finger grippable lever 158, and plunger stem 168 of apparatus 150 may be formed by injection molding a suitable plastic material. Exemplary materials include, but are not limited to acrylonitrile butadiene styrene and/or polyphenylsulphone. Polyphenylsulphone is particularly preferred, as it can be autoclaved many times while still retaining structural integrity (e.g., 100 or more cycles). Handle 154, the support member (e.g., cradle 156), lever 158, and plunger stem 168 may be formed of a material that is easily cleaned, so as to minimize the risk of cross-contamination between patients. Cleaning may be accomplished by wiping down or otherwise washing the handle, cradle, plunger stem, and lever, or by autoclaving these portions. Hollow suction tube 160 is advantageously separable from the remainder of the apparatus so as to be disposable, which also acts to minimize risk of cross-contamination between patients, particularly as tube 160 is the part of the apparatus most likely to touch bodily fluids of a patient. As plunger 166 is also detachable from the remainder of apparatus 150, it is also possible for the plunger to be disposed of (rather than cleaned) after a single use also, if desired.

Figure 7A:
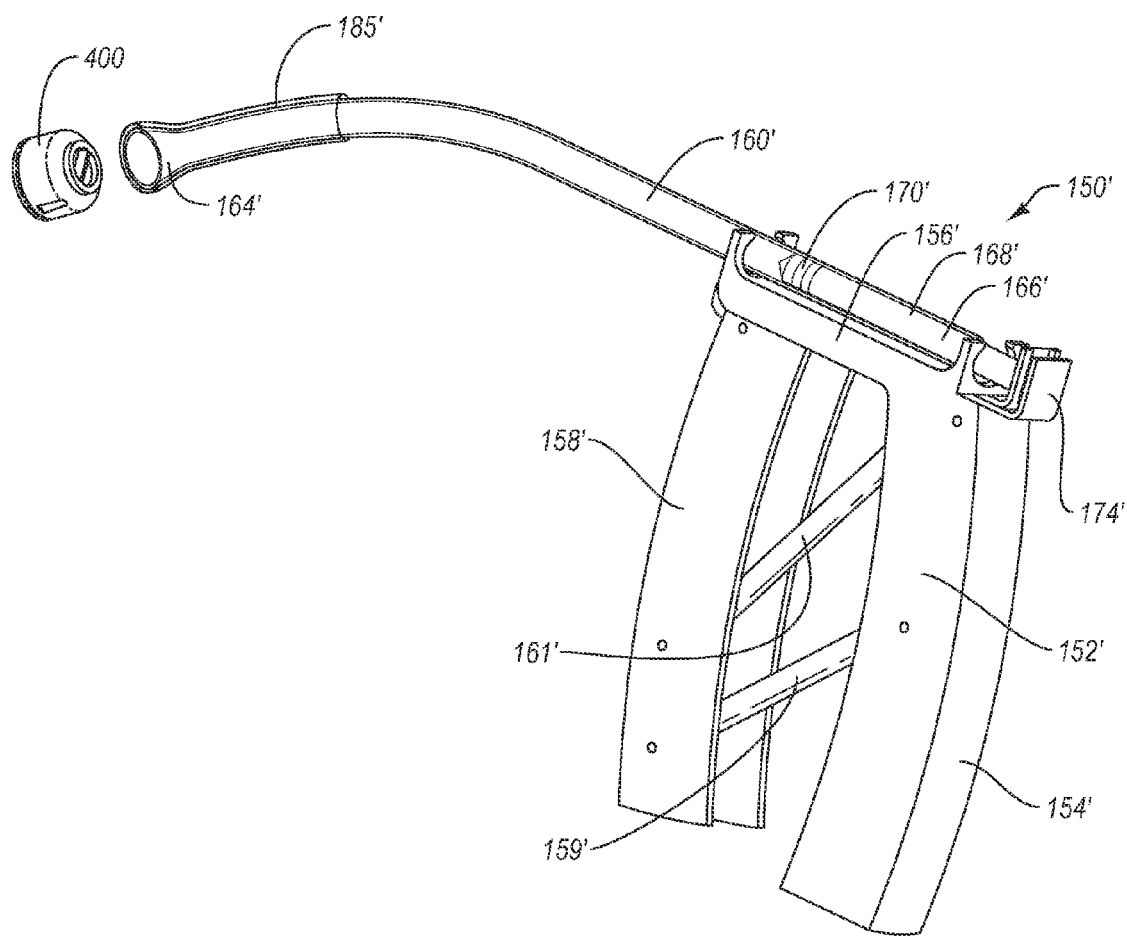
FIG. 7A is a perspective view of an alternative hand-held vacuum pump apparatus for use in attaching a saliva control device over a salivary duct.
Figure 7B:
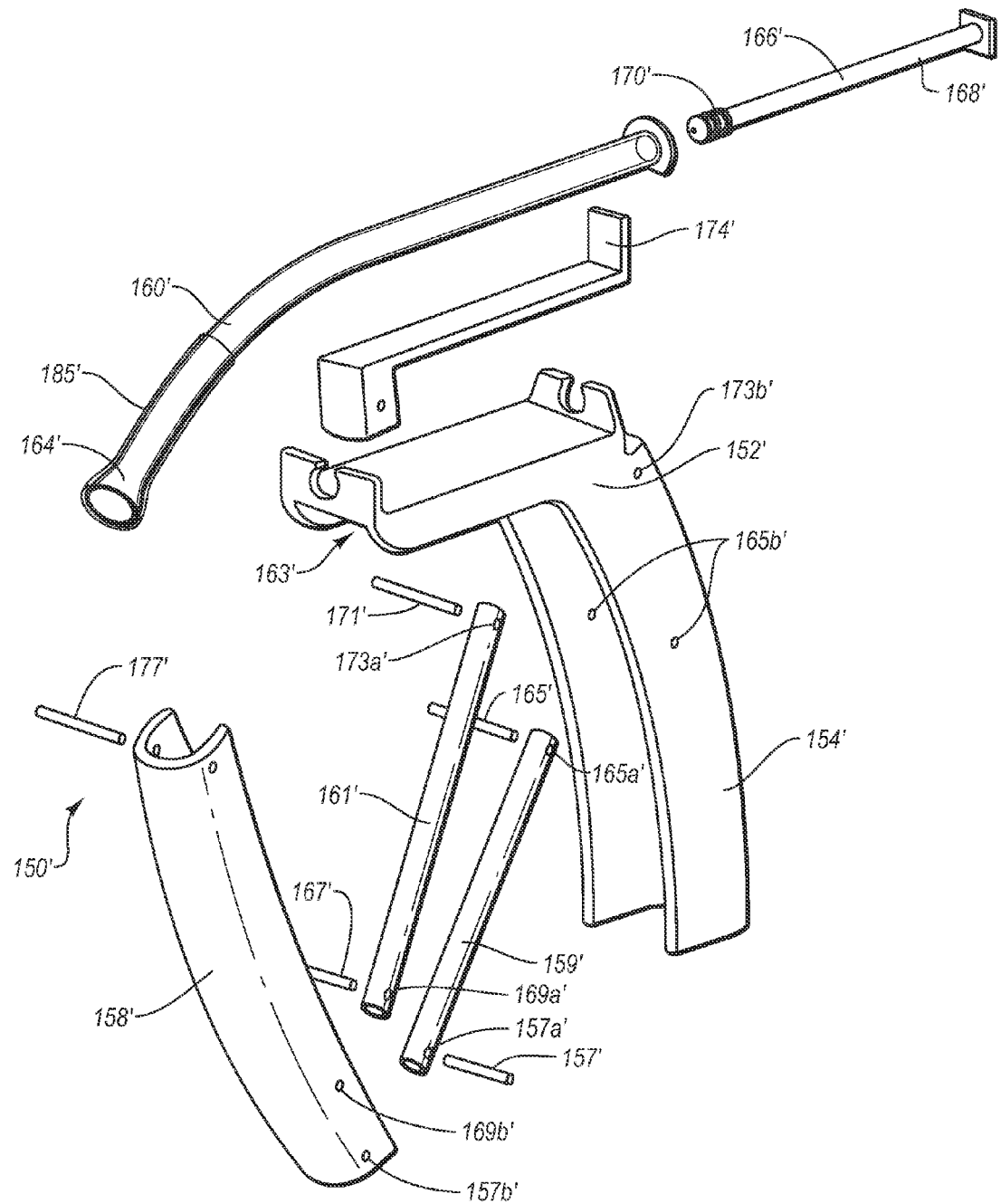
FIG. 7B is an exploded view of the vacuum pump apparatus of FIG. 7A.

FIGS. 7A-7B illustrate an alternative apparatus 150' including a body 152' having a grippable handle 154' and a support member 156'. A finger grippable lever 158' is substantially parallel to and spaced distally apart from grippable handle 154'. In use, the practitioner is able to pull lever 158' towards handle 154' (e.g., by squeezing the hand and/or at least one finger). The substantially parallel configuration of lever 158' relative to handle 154' facilitates easy gripping of both the handle and lever with a single hand, and provides for efficient, simple, and comfortable single hand operation. A hollow suction tube 160' is supported by support member 156', and a plunger 166' is slidably disposed within hollow suction tube 160'. In the illustrated embodiment, tube 160' extends far beyond the distal end of support member 156', and as such, tube 160' may be formed of a more rigid material as compared to tube 160, which is almost completely supported by cradle support member 156.

In the illustrated embodiment, lever 158' is connected to handle 154' by first and second support members 159' and 161', respectively. Each of support members 159' and 161' is pivotally connected at each end, i.e., one end of each support member is pivotally connected to lever 158', while the other end of each support member is pivotally connected to handle 154' such that lever 158' and handle 154' are substantially parallel. Support member 159' is pivotally connected at one end to lever 158' by a pin 157', while the opposite end of support member 159' is pivotally connected to handle 154' by another pin 165'. Pin 157' passes through a pair of holes 157*a'* formed near an end of support member 159', and end sections of pin 157' may be retained within a pair of holes 157*b'* formed within lever 158'. Pin 165' passes through a pair of holes 165*a'* formed near an opposite end of support member 159', and end sections of pin 165' may be retained within a pair of holes 165*b'* formed within handle 154'. Support member 161' is pivotally connected to lever 158' and handle 154' in a similar manner. Pin 167' passes through a pair of holes 169*a'* formed near an end of support member 161', and end sections of pin 167' may be retained within a pair of holes 169*b'* formed within lever 158'. Another pin 171' passes through a pair of holes 173*a'* formed near an opposite end of support member 161', and end sections of pin 171' may be retained within a pair of holes 173*b'* formed within handle 154'. Other attachment configurations will be apparent to one skilled in the art.

When a practitioner pulls lever 158' towards handle 154', lever 158' slides proximally towards handle 154'. In addition to support members 159' and 161', the sliding movement of lever 158' is guided by a channel 163' formed within body 152' so as to result in a smooth and guided feel for the practitioner during use. Such a smooth and guided feel is advantageous as it allows the practitioner to concentrate on positioning and placement of the saliva control device rather than the operation of the vacuum pump apparatus.

Plunger 166' includes a stem 168' and a sealing plug 170'. A proximal end of stem 168' is attached to a coupler 174' that is attached to lever 158' (e.g., at a distal end of element 174' by pin 177'). In use, when the practitioner holds handle 154' and squeezes lever 158', lever 158' is pulled towards handle 154'. Coupler 174' moves proximally, pulling plunger 166' proximally within hollow suction tube 160', which results in the creation of a vacuum within hollow suction tube 160'. Release of lever 158' allows distal movement of sealing plug 170', which releases the vacuum. Coupler 174' is another example of coupling means for operatively coupling the plunger 166' to lever 158'.

Distal end 164' of tube 160' may advantageously be configured to couple with or otherwise mate with a saliva control device to be installed. For example, the distal end 164' of hollow suction tube 160' may be configured to friction fit over a raised rim, hub or protrusion formed on the top of saliva control device 400, as illustrated (FIG. 7A). Of course, distal end 164' may be configured to mate with saliva control device 100 of FIG. 1, or with any other saliva control device. Other configurations of distal end 164' for coupling or attaching to a saliva control device will be apparent to those skilled in the art.

In one embodiment, tube 160' may advantageously include an outer tube 185' which is slidably disposed over hollow suction tube 160' for forcing device 400 off distal end 164' once the saliva control device is in the desired position. Tweezers, the practitioner's fingers, or another dental tool may alternatively be used to slide and/or push device 400 distally off distal end 164'. Although illustrated in conjunction with apparatus 150', it will be understood that a slidable outer tube (e.g., tube 185') may be included with any of the illustrated hand-held vacuum pump apparatuses. For example, such a slidable outer tube may be included with device 150 of FIGS. 5-6. After positioning the saliva control device as needed over a salivary duct, the outer tube may be used to force a saliva control device (e.g., device 100) over and/or off distal end 164 (e.g., constriction hole 104 of device 100 may be stretched so as to initially position device 100 over tube 160, and an outer tube may be used to push device 100 over distal end 164). Once device 100 is slid off distal end 164, elastic body 102 springs closed because of the elasticity of elastic body 102 surrounding constriction hole 104. The result is that the base of the tissue nub surrounding the salivary duct becomes inserted through constriction hole 104. The vacuum within hollow suction tube 160 may then be released.

Figure 8:
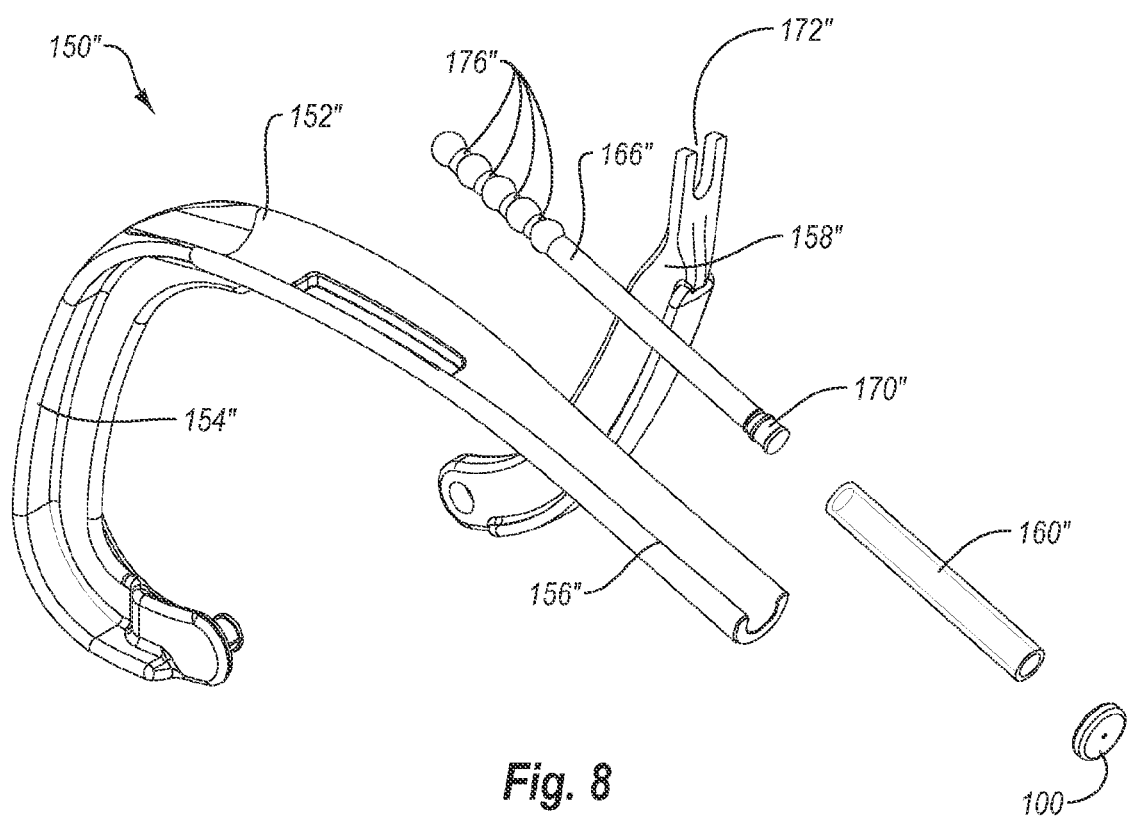
FIG. 8 is a perspective view of another alternative vacuum pump apparatus.

FIG. 8 illustrates another alternative hand-held vacuum pump apparatus 150" including a body 152" having a grippable handle 154" and a support member 156". A finger grippable lever 158" is substantially parallel to and spaced distally apart from grippable handle 154". In use, the practitioner is able to pull lever 158" towards handle 154" (e.g., by squeezing the hand and/or at least one finger). A hollow suction tube 160" is supported by support member 156", and a plunger 166" is slidably disposed within hollow suction tube 160".

Apparatus 150" is similar to apparatus 150 of FIGS. 5-6, with a principal difference being the means for coupling plunger 166" to lever 158". Plunger 166" is operatively coupled at its proximal end to lever 158". In the illustrated embodiment, plunger 166" is not smooth, but rather includes a series of indented locking positions 176" for engagement with a fork 172" disposed at an end of lever 158". The practitioner is advantageously able to adjust the force of the vacuum generated by selecting which locking position fork 172" is engaged in, which adjusts the length of displacement of plunger 166" for any given locking position. Adjustability of the force of the produced vacuum is advantageous as it allows the practitioner to select and deliver a sufficient vacuum force to enable adhering the saliva control device over a salivary duct, while also minimizing any discomfort of the patient as a result of application of a very strong vacuum force, which may be uncomfortable.

This coupling configuration of lever 158" and plunger 166" provides that selective movement of lever 158" (i.e., pulling it towards handle 154") causes plug 170" of plunger 166" to slide proximally within hollow suction tube 160" so as to create a vacuum within tube 160". The vacuum can be released by releasing lever 158", permitting distal movement of plug 170" of plunger 166" within tube 160".

Figure 9:
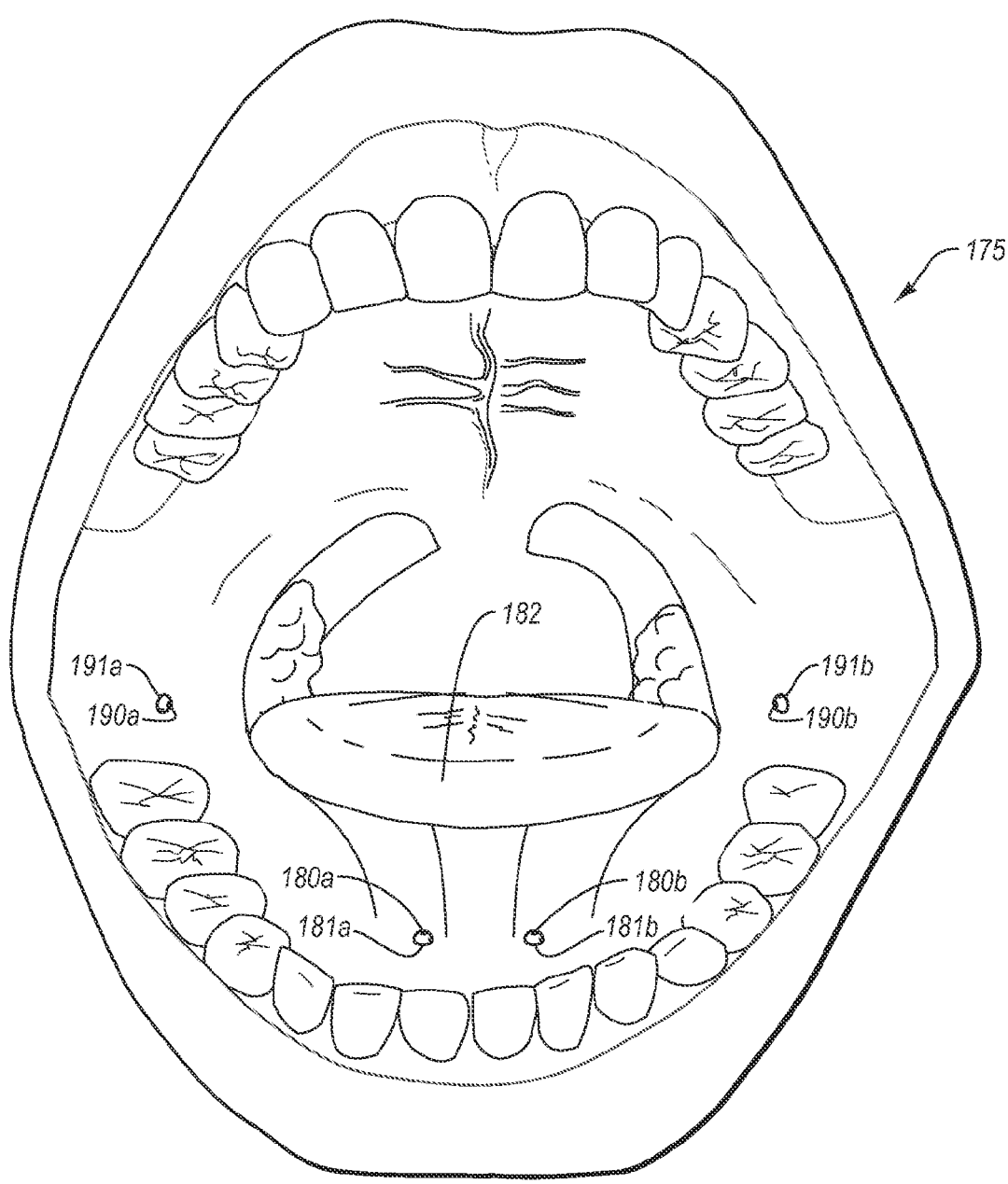
FIG. 9 illustrates the inside of a patient's mouth including the two submandibular salivary ducts on the floor of the mouth.

FIGS. 9 and 10A-10B illustrate a method of using the apparatus 150 of FIG. 5 to install a saliva control device over one or more of a patient's salivary ducts. Referring to FIG. 9, the two submandibular salivary ducts 180a and 180b, which are normally covered by the tongue 182, are seen on the floor of the mouth of patient 175. Each duct 180a and 180b is surrounded by a raised nub of tissue 181a and 181b, respectively. The two parotid salivary ducts 190a and 190b and their associated tissue nubs 191a and 191b are also visible on the inside of the patient's cheeks. As illustrated in FIG. 10A, saliva control device 100 is fitted over the distal end of hollow suction tube 160 of suction apparatus 150. Saliva control device 100 is then positioned over a selected salivary duct and raised tissue nub (e.g., nub 181a). A vacuum is applied to hollow suction tube 160 so as to cause tissue nub 181a surrounding salivary duct 180a to be pulled up into hollow suction tube 160. Where device 100 is friction fitted with a distal end of hollow suction tube 160 as described above, the vacuum is also applied through constriction hole 104, and tissue nub 181a becomes inserted through constriction hole 104 and into suction tube 160. Once tissue nub 181a is inserted through constriction hole 104, the vacuum of suction apparatus 150 can be released and apparatus 150 can be removed.

An adhesive, anesthetic, and/or lubricant may be applied (e.g., either pre-applied during manufacture of the saliva control device or applied just prior to use) to an underside of device 100 prior to positioning of the device over the salivary duct. An adhesive may be helpful in keeping the device in place, particularly for relatively long time periods (e.g., greater than 90 minutes). Examples of suitable oral adhesives that can adhere to moist oral tissue include polyvinylpyrrolidone, carboxymethylcellulose, carbopol, or a light curable adhesive (e.g., a hydrophilic polyurethane, a hydrophilic acrylic, or a hydrophilic polyurethane-acrylic). An anesthetic (e.g., benzocaine) or a lubricant may advantageously be applied to an underside of device 100 to reduce any discomfort felt by the patient as a result of the constriction around the salivary ducts to which control devices are applied.

As seen in FIG. 10B, elastic body 102 surrounding constriction hole 104 constricts around tissue nub 181a surrounding salivary duct 180a. Tissue nub 181a may protrude out the top of constriction hole 104. Constriction hole 104 is of a sufficiently small diameter and the stiffness and stretchability of the material from which elastic body 102 is formed is such so as to constrict around salivary duct 180a such that production and flow of saliva from salivary duct 180a is prevented. Preferably, the diameter of constriction hole 104 and the stiffness and stretchability of the material of elastic body 102 is formed is such so as to constrict around salivary duct 180a such that production and flow of saliva from salivary duct is prevented. Preferably, the diameter of construction hole 104 and the stiffness and stretchability of the material of elastic body 102 is not so tight so as to substantially prevent the flow of blood through tissue nub 181a surrounding salivary duct 180a. In other words, tissue nub 181a may advantageously remain red and vital throughout the procedure while device 100 is in place so as to not permanently damage the patient's tissue. Although the method is illustrated with respect to one particular saliva control device 100 and salivary duct 180*a*, it is to be understood that any one or more of the four principal salivary ducts may be selected for attachment of a saliva control device. Furthermore, it is to be understood that the various other saliva control devices (e.g., device 400) may be installed in lieu of device 100. Tube 160 may be used with a single patient to install as many devices as desired, after which it may be discarded. The plunger may also be discarded, or cleaned, along with the body and lever of the apparatus prior to use with another patient.

The saliva control device may remain in place as long as necessary, typically between about 10 minutes and about 3 hours, more typically between about 20 minutes and about 2.5 hours, and most typically between about 30 minutes and about 2 hours, after which the saliva control device or devices are removed (e.g., by prying them off with pliers, a dental tool or even a fingernail). The raised rim 106 (FIG. 1) assists in gripping of the device for removal. As described above in conjunction with FIGS. 2, 3A, 3B, and 3C, the saliva control device may advantageously include alternative means for providing a gripping surface for facilitating removal of the device (e.g., the elastic body may include one or more ear-like protrusions, one or more slits, or one or more cut-outs to provide an edge or gripping surface which can be more easily gripped by the practitioner so as to allow for easy removal of the device when desired).

It will be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A saliva control device for attachment to a salivary duct and configured to prevent flow of saliva from a salivary duct without damaging the salivary duct and surrounding soft oral tissue, the saliva control device comprising:
    an elastic body comprising at least one elastomer and having a bottom surface for placement against oral tissue surrounding a salivary duct;
    a constriction hole having a diameter and formed through the elastic body; and
    an interior wall in the elastic body defining the constriction hole,
    wherein the interior wall is substantially smooth,
    wherein the elastic body has an elasticity and stiffness which cooperate with the diameter of the constriction hole so that, during use of the saliva control device to prevent saliva from flowing from a salivary duct, the constriction hole can expand during placement around a salivary duct and the interior wall can constrict around the salivary duct to prevent flow of saliva without substantially cutting off blood flow to the salivary duct and soft oral tissue surrounding the salivary duct so as to not damage and kill the salivary duct and the soft oral tissue surrounding the salivary duct.

2. A saliva control device as recited in claim 1, wherein the diameter of the constriction hole is in a range of about 0.1 mm to about 2 mm.

3. A saliva control device as recited in claim 1, wherein the diameter of the constriction hole is in a range of about 0.5 mm and about 1.75 mm.

4. A saliva control device as recited in claim 1, wherein the diameter of the constriction hole is in a range of about 0.8 mm and about 1.5 mm.

5. A saliva control device as recited in claim 1, wherein the at least one elastomer has a stretchability of at least about 200 percent.

6. A saliva control device as recited in claim 1, wherein the at least one elastomer has a stretchability of at least about 400 percent.

7. A saliva control device as recited in claim 1, wherein the at least one elastomer has a stretchability of at least about 800 percent.

8. A saliva control device as recited in claim 1, wherein the at least one elastomer has a stretchability of at least about 500 percent and the constriction hole has a diameter less than about 0.8 mm.

9. A saliva control device as recited in claim 1, further comprising means for providing a gripping surface on the elastic body for facilitating removal of the saliva control device from a salivary duct.

10. A saliva control device as recited in claim 9, wherein the means for providing a gripping surface on the elastic body comprises at least one of:
    a raised rim extending around an outer perimeter of the elastic body;
    one or more ear-like protrusions;
    a slit extending from an outer edge of the elastic body towards but not to the opening; or
    a cut-out extending from an outer edge of the elastic body towards but not to the opening.

11. A saliva control device as recited in claim 1, wherein the at least one elastomer comprises one or more of a thermoplastic elastomer, a polyolefin, latex, or a styrene-ethylene-butylene-styrene.

12. A saliva control device as recited in claim 1, wherein the elastic body comprises a substantially flat disc.

13. A saliva control device as recited in claim 1, wherein the elastic body is substantially circular, oval or rectangular.

14. A saliva control device as recited in claim 1, further comprising a vacuum chamber defined within the elastic body in fluid communication with the constriction hole so that, upon applying a vacuum to the vacuum chamber, the applied vacuum assists in pulling a salivary duct through the constriction hole in order to constrict and seal the salivary duct within the constriction hole.

15. A saliva control device as recited in claim 14, further comprising an air evacuation passage in fluid communication with the vacuum chamber through which a vacuum can be applied to the vacuum chamber, the air evacuation passage comprising a one-way valve for sealing the evacuation passage after the vacuum has been applied.

16. A system as recited in claim 15, wherein the air evacuation passage comprises a one-way slit valve.

17. A saliva control device for attachment to a salivary duct and configured to prevent flow of saliva from a salivary duct without damaging the salivary duct and surrounding soft oral tissue, the saliva control device comprising:
    an elastic body comprising at least one elastomer having a stretchability of at least about 200 percent, the elastic body having a bottom surface for placement against oral tissue surrounding a salivary duct;
    a constriction hole formed through the elastic body and having a diameter in a range of about 0.1 mm to about 2 mm; and
    an interior wall in the elastic body defining the constriction hole,
    wherein the interior wall is substantially smooth, wherein the elastic body has an elasticity and stiffness which cooperate with the diameter of the constriction hole so that, during use of the saliva control device to prevent saliva from flowing from a salivary duct, the constriction hole can expand during placement around a salivary duct and the interior wall can constrict around the salivary duct to prevent flow of saliva without substantially cutting off blood flow to the salivary duct and soft oral tissue surrounding the salivary duct so as to not damage and kill the salivary duct and the soft oral tissue surrounding the salivary duct.

18. A saliva control device as recited in claim 17, wherein the at least one elastomer has a stretchability of at least about 400 percent and the constriction hole has a diameter in a range of about 0.5 mm and about 1.75 mm.

19. A saliva control device for attachment to a salivary duct and configured to prevent flow of saliva from a salivary duct without damaging the salivary duct and surrounding soft oral tissue, the saliva control device comprising:

an elastic body comprising at least one elastomer and having a bottom surface for placement against oral tissue surrounding a salivary duct;

a raised rim extending around an outer perimeter of that elastic body that facilitates removal of the elastic body from a salivary duct, increases rigidity of the elastic body, and is configured to form a friction fit with a hollow suction tube used to install the saliva control device around a salivary duct;

a constriction hole formed through the elastic body; and an interior wall in the elastic body defining the constriction hole, wherein the interior wall is substantially smooth and the elastic body has an elasticity and stiffness so that, during use of the saliva control device, the constriction hole can expand during placement around a salivary duct and the interior wall can constrict around the salivary duct to prevent flow of saliva without substantially cutting off blood flow to and damaging the salivary duct and soft oral tissue surrounding the salivary duct.

20. A saliva control device as recited in claim 19, wherein the at least one elastomer has a stretchability of at least about 200 percent and the constriction hole has a diameter in a range of about 0.1 mm and about 2 mm.

* * * * *

UNITED STATES PATENT AND TRADEMARK OFFICE
CERTIFICATE OF CORRECTION

| | |
|---|---|
| PATENT NO. | : 8,353,701 B2 |
| APPLICATION NO. | : 12/857659 |
| DATED | : January 15, 2013 |
| INVENTOR(S) | : Odenkirchen |

It is certified that error appears in the above-identified patent and that said Letters Patent is hereby corrected as shown below:

In the Specification

Column 4
Line 21, change "full" to --fully--

Column 8
Line 40, change "460" to --560--

Column 10
Line 2, change "digital" to --distal--

Column 14
Line 51, change "181 a" to --181a--
Line 52, change "181 a" to --181a--
Line 56, change "is such so as to" to --so as to--
Line 60, change "is such so as to" to --so as to--
Line 64, change "tight so as to" to --tight as to--
Line 65, change "181 a" to --181a--
Line 66, change "181 a" to --181a--

Signed and Sealed this
Twenty-fourth Day of September, 2013

Teresa Stanek Rea
*Deputy Director of the United States Patent and Trademark Office*